United States Patent [19]

Johnson, Jr.

[11] Patent Number: 4,551,570
[45] Date of Patent: Nov. 5, 1985

[54] PROCESS FOR THE ISOMERIZATION OF LIMONENE TO TERPINOLENE

[75] Inventor: Walter E. Johnson, Jr., Jacksonville, Fla.

[73] Assignee: SCM Corporation, New York, N.Y.

[21] Appl. No.: 691,412

[22] Filed: Jan. 14, 1985

[51] Int. Cl.⁴ ............................................. C07C 5/30
[52] U.S. Cl. .................................. 585/355; 585/353; 585/377; 585/947
[58] Field of Search ............... 585/355, 377, 353, 378, 585/947

[56] References Cited

U.S. PATENT DOCUMENTS

| | | | |
|---|---|---|---|
| 1,985,792 | 12/1934 | Meerwin et al. | 585/355 |
| 2,097,743 | 11/1937 | Sheffield | 585/355 |
| 3,700,746 | 10/1972 | Takacs | 585/355 |
| 3,700,747 | 10/1972 | Takacs | 585/377 |
| 3,780,124 | 12/1973 | Davis | 585/355 |

*Primary Examiner*—D. E. Gantz
*Assistant Examiner*—A. Pal
*Attorney, Agent, or Firm*—R. A. Sturges; T. M. Schmitz

[57] ABSTRACT

A process for isomerizing limonene to terpinolene in the presence of an acidic catalyst and in the presence of a buffer.

8 Claims, No Drawings

PROCESS FOR THE ISOMERIZATION OF LIMONENE TO TERPINOLENE

This invention relates to an isomerization process and more particularly to the isomerization of limonene to terpinolene.

BACKGROUND OF THE INVENTION AND PRIOR ART

Terpinolene, or para-mentha-1,4(8)-diene, is a terpenoid hydrocarbon. It has a sweet-piney, oily and relatively pleasant odor. It is used as a fragrance providing ingredient for household cleansers, in deodorizers, "reodorants", masking agents, etc. It is also useful as a starting material for the preparation of terpineol, or 1-methyl-4-isopropylidene cyclohexanol-1. It is also used as a chain terminating agent in certain aqueous polymerizations. Industrial demand has increased giving rise to a need for a more efficient process for producing terpinolene and minimizing the production of concomitant by-products.

Catalytic isomerization of (+)-transisolimonene to optically active (+)-isoterpinolene has been carried out using high surface sodium on alumina which has been partially deactivated. Partial deactivation limits the production of p-cymene, an undesired product of lesser value. (See Indian Pat. No. 146,086 filed June 26, 1976).

Metatitanic acid has been used as a catalyst in the isomerization of 2-carane oxide to cis-isolimonenol (See U.S. Pat. No. 3,814,733 to Bledsoe et al. It has also been used to isomerize dipentene and terpinolene although yields of terpinolene from dipentene were low (21%) and not as high as with ohydroxy benzoic acid catalyst (Chem. Abst. 81(13)78097d).

It has now been found that orthotitanic acid is an effective catalyst in terms of selectivity and conversion for the selective isomerization of limonene to terpinolene provided the reaction is carried out in the presence of a small amount of an alkali metal alkaline earth metal or ammonium salt of a weak acid as a buffer, e.g., sodium acetate.

BRIEF STATEMENT OF THE INVENTION

Briefly stated, therefore, the present invention is a process for isomerizing limonene to terpinolene in the presence of a catalytic amount of orthotitanic acid (Reg. No. 20338-08-3) at a temperature from 75 degrees C. to 150 degrees C. which process is characterized by the presence in the isomerization mass of from 0.05% to 2% or more by weight of the limonene charge of a buffer. The time of reaction under isomerization conditions is not critical and is, in general, that which is sufficient to effect the desired conversion and selectivity, and as exemplified in the Tables below.

DETAILED DESCRIPTION AND SPECIFIC EXAMPLES

When it was sought to isomerize limonene to terpinolene using orthotitanic acid as a catalyst in undiluted limonene, it was found that the reaction was wildly exothermic to 215 degrees C. yielding principally p-cymene. The use of a hydrocarbon solvent, e.g., heptane was found to hold the temperature to 105 degrees C. However, after a few hours, few diene components were found, with mostly dimers and higher polymers being obtained. It was then decided to utilize a material normally regarded as a buffer in effort to moderate the reaction. This proved to be successful in that it allowed control of the reaction easily at 100 degrees C. without exotherm. No solvent was necessary. Sodium acetate as a reaction control agent was found to be especially effective at concentrations of from 0.1% to 1.0% by weight of the limonene charge, and more particularly from 0.2% to 0.5% by weight. Higher amounts of the control agent or buffer appear not to improve the conversion or selectivity and thus, the upper limit of concentration is not critical. The lower limit appears to be about 0.05% by weight of the limonene charge. At levels of 0.2% and 0.5% sodium acetate buffer, excellent results were obtained at 100 degrees C. With 0.5%, after 4 hours, 55% conversion gave 70% selectivity of terpinolene. At 0.2%, after 4 hours 55% conversion gave 69% selectivity. The catalyst was solid orthotitanic acid. The foregoing conversions and selectivities are commercially acceptable.

The catalyst is apparently poisoned in the reaction, possibly by the buffer, and cannot be recovered for reuse without regeneration.

A number of examples for comparative purposes have been carried out following a standardized isomerization procedure. The isomerization reaction was carried out in a 500 cc vessel using a charge of 250 cc of limonene (211 grams); 2 grams of solid orthotitanic acid conditioned at 150 degrees C. (W-91 in the tables below); and the buffer. The mixture was heated slowly under nitrogen atmosphere to 100 degrees C. (or 140 degrees C. as specified) and for various times ranging from 1 to 21.5 hours. The product was analyzed by conventional methods, the conversion and selectivity for terpinolene and the amounts of other products determined. The following tables are believed self-explanatory in the light of the foregoing.

TABLE I

| SAMPLE NO. | CHARGE | 1 | 2 | 3 | 4 | 5 | 6 | 7 | 8 | 9 | 10 | 11 | 12 | 13 |
|---|---|---|---|---|---|---|---|---|---|---|---|---|---|---|
| Orthotitanic Acid | 0.95 | | | | | | | | | | | | | |
| % NaAcetate | 0.19 | | | | | | | | | | | | | |
| Time | | 2 | 3 | 4 | 5 | 6 | 7.5 | 9.5 | 11.5 | 13.5 | 15.5 | 17.5 | 19.5 | 21.5 |
| % alpha-Terpinene | | 4.25 | 5.49 | 6.12 | 6.43 | 6.65 | 6.89 | 7.11 | 7.24 | 7.28 | 7.29 | 7.24 | 7.30 | 7.30 |
| % p-cymene | | 0.29 | 0.29 | 0.29 | 0.29 | 0.30 | 0.31 | 0.34 | 0.35 | 0.35 | 0.35 | 0.36 | 0.36 | 0.37 |
| % Limonene | 98.75 | 57.73 | 49.70 | 46.09 | 43.92 | 42.96 | 41.35 | 39.90 | 39.53 | 39.27 | 39.09 | 38.56 | 38.48 | 38.32 |
| % gamma-terpinene | | 4.12 | 5.61 | 6.40 | 6.81 | 7.10 | 7.32 | 7.73 | 7.90 | 7.94 | 8.01 | 8.05 | 8.10 | 8.14 |
| % 3,8-9 menthadiene | | 0.21 | 0.30 | 0.37 | 0.37 | 0.39 | 0.41 | 0.43 | 0.44 | 0.44 | 0.45 | 0.46 | 0.46 | 0.46 |
| % Terpinolene | | 31.11 | 35.45 | 37.17 | 38.06 | 38.54 | 39.30 | 39.45 | 39.85 | 39.89 | 40.05 | 40.51 | 40.45 | 40.53 |
| % 2,4-8 p-menthadiene | | 1.71 | 2.42 | 2.80 | 3.10 | 3.21 | 4.42 | 3.54 | 3.64 | 3.68 | 3.76 | 3.79 | 3.82 | 3.84 |
| % Conversion | | 41.54 | 49.67 | 53.33 | 55.52 | 56.50 | 58.13 | 59.59 | 59.97 | 60.23 | 60.42 | 60.95 | 61.03 | 61.19 |
| % Selectivity Terpinolene | | 75.84 | 72.27 | 70.58 | 69.41 | 69.08 | 68.47 | 67.03 | 67.29 | 67.06 | 67.13 | 67.30 | 67.11 | 67.09 |

The amount of sodium acetate buffer was 0.4 grams and the temperature was 100 degrees C., which is a preferred reaction temperature. Lower temperatures down to about 75 degrees C., may be used. However, the time is unduly extended. Above about 150 degrees C. the conversion appears to increase, but the selectivity for terpinolene tends to fall off.

It will be observed in the foregoing Table I that the production of p-cymene and various dienes is very low. Conversion and selectivity for terpinolene are commercially acceptable and a large portion of the isomerizate is unreacted limonene which can be recovered and recycled. Fresh catalyst and buffer can be added along with make up limonene and the reaction continued. It is also of interest to note that the production of undesirable by-products tends to increase with time with optimum results occuring between 3 and 4 hours of isomerization time with the quantities of reactant, catalyst and buffer used.

In Table II, the amount of buffer is increased by 2.5 times to 0.47%. The isomerization time is up to 6 hours. Again optimum results are achieved between 3 and 4 hours.

TABLE II

| SAMPLE NO. | CHARGE | 1 | 2 | 3 | 4 | 5 |
|---|---|---|---|---|---|---|
| Orthotitanic Acid | 0.95 | | | | | |
| % NaAc | 0.47 | | | | | |
| Time | | 2 | 3 | 4 | 5 | 6 |
| % alpha-terpinene | | 3.80 | 4.43 | 5.30 | 6.28 | 7.14 |
| % p-cymene | | 0.14 | 0.17 | 0.21 | 0.27 | 0.34 |
| % Limonene | 98.75 | 60.19 | 55.44 | 50.28 | 44.85 | 40.51 |
| % gamma-terpinene | | 3.64 | 4.38 | 5.41 | 6.57 | 7.67 |
| % 3,8-9-menthadiene | | 0.19 | 0.23 | 0.29 | 0.35 | 0.41 |
| % terpinolene | | 29.69 | 32.57 | 35.37 | 37.70 | 39.51 |
| % 2,4-8-menthadiene | | 1.49 | 1.89 | 2.36 | 2.91 | 3.42 |
| % Conversion | | 39.05 | 43.86 | 49.08 | 54.58 | 58.98 |
| % Selectivity Terpinolene | | 77.00 | 75.20 | 72.97 | 69.94 | 67.84 |

The foregoing tables have shown the effectiveness of sodium acetate as a buffer or control agent for the isomerization of limonene to terpinolene. Numerous other buffer materials have been tried and found to yield reasonable selectivities over a wide range of conversion percentages. The following Table III set forth the weight of the buffer in grams, the isomerization temperature, the sample number, the time in hours and the amount of various products identified in the isomerizate. The % conversion and selectivity for gamma-terpinene and terpinolene is given also. In each case, 211 grams of limonene were used along with 2 grams of orthotitanic acid. The time for isomerization was uniformly held at 4 hours, an optimum time for the conditions obtaining in accordance with Tables I and II above.

TABLE III (Part 1)

| Buffer | Wt. of Buffer | Temp. Degrees C. | % 1 alpha-terpinene | % 2 p-cymene | % Limonene | % 3 gamma-terpinenes | % 4 2,4-8-menthadiene | terpinolene |
|---|---|---|---|---|---|---|---|---|
| NaAc | 0.3 | 100 | 3.44 | 0.87 | 77.59 | 2.98 | 1.12 | 12.56 |
| NaAc | 0.3 | 140 | 28.71 | 9.32 | 3.81 | 21.22 | 15.56 | 7.85 |
| KAc | 0.3 | 100 | 1.10 | 0.49 | 92.78 | 1.04 | 0.33 | 3.49 |
| KAc | 0.3 | 140 | 1.87 | 0.77 | 88.42 | 1.76 | 0.76 | 5.29 |
| NH4Ac | 0.3 | 100 | 0.40 | 0.31 | 97.24 | 0.43 | 0.15 | 0.95 |
| NH4Ac | 0.3 | 140 | 0.55 | 0.39 | 96.30 | 0.59 | 0.27 | 1.33 |
| Ca(Ac)2 | 0.3 | 100 | 2.34 | 0.75 | 86.07 | 2.11 | 0.77 | 6.93 |
| Ca(Ac)2 | 0.3 | 140 | 8.83 | 2.32 | 56.65 | 7.06 | 3.86 | 17.57 |
| LiAc | 0.3 | 100 | 2.50 | 0.60 | 83.44 | 2.08 | 0.77 | 9.90 |
| LiAc | 0.3 | 140 | 26.12 | 4.93 | 9.90 | 20.59 | 13.26 | 16.54 |
| Ba(Ac)2 | 0.3 | 100 | 2.84 | 0.81 | 81.95 | 2.64 | 1.01 | 9.40 |
| Ba(Ac)2 | 0.3 | 140 | 19.20 | 4.57 | 23.11 | 15.07 | 8.41 | 22.35 |
| NaHCO3 | 0.3 | 100 | 3.37 | 0.89 | 78.87 | 3.16 | 1.25 | 11.02 |
| NaHCO3 | 0.3 | 140 | 25.47 | 5.99 | 11.27 | 19.44 | 11.69 | 17.00 |
| KHCO3 | 0.3 | 100 | 2.47 | 0.54 | 84.43 | 2.15 | 0.87 | 8.94 |
| KHCO3 | 0.3 | 140 | 20.07 | 3.98 | 20.56 | 15.86 | 9.60 | 23.02 |
| NH4HCO3 | 0.3 | 100 | 0.63 | 0.38 | 96.05 | 0.64 | 0.20 | 1.58 |
| NH4HCO3 | 0.3 | 140 | 0.71 | 0.43 | 95.49 | 0.72 | 0.27 | 1.82 |
| Na2CO3 | 0.3 | 100 | 3.25 | 0.75 | 79.84 | 2.62 | 1.07 | 11.40 |
| Na2CO3 | 0.3 | 140 | 28.91 | 8.92 | 3.90 | 22.52 | 15.31 | 7.73 |
| K2CO3 | 0.3 | 100 | 0.66 | 0.32 | 95.60 | 0.63 | 0.23 | 2.19 |
| K2CO3 | 0.3 | 140 | 1.72 | 0.71 | 91.13 | 1.37 | 0.66 | 3.47 |

(Part 2)

| Buffer | % Conversion | % 1 alpha-terpinene | % 2 p-cymene | % Selectivity for 3 & 5 | % 3 gamma-terpinene | % 4 2,4-8-menthadiene | % 5 terpinolene |
|---|---|---|---|---|---|---|---|
| NaAc | 22.25 | 15.46 | 3.91 | 69.84 | 13.39 | 5.03 | 56.45 |
| NaAc | 96.03 | 29.90 | 9.71 | 30.27 | 22.10 | 16.20 | 8.17 |
| KAc | 7.06 | 15.58 | 6.94 | 64.16 | 14.73 | 4.67 | 49.43 |
| KAc | 11.42 | 16.37 | 6.74 | 61.73 | 15.41 | 6.65 | 46.32 |
| NH4Ac | 2.60 | 15.38 | 11.92 | 63.08 | 16.54 | 5.77 | 36.54 |
| NH4Ac | 3.54 | 15.54 | 11.02 | 54.24 | 16.67 | 7.63 | 37.57 |
| Ca(Ac)2 | 13.77 | 16.99 | 5.45 | 65.65 | 15.32 | 5.59 | 50.33 |
| Ca(Ac)2 | 43.19 | 20.44 | 5.37 | 57.03 | 16.35 | 8.94 | 40.68 |
| LiAc | 16.40 | 15.24 | 3.66 | 73.05 | 12.68 | 4.70 | 60.37 |
| LiAc | 89.94 | 29.04 | 5.48 | 41.28 | 22.89 | 14.74 | 18.39 |
| Ba(Ac)2 | 17.89 | 15.87 | 4.53 | 67.30 | 14.76 | 5.65 | 52.54 |
| Ba(Ac)2 | 76.73 | 25.02 | 5.96 | 48.77 | 19.64 | 10.96 | 29.13 |
| NaHCO3 | 20.97 | 16.07 | 4.24 | 67.62 | 15.07 | 5.96 | 52.55 |
| NaHCO3 | 88.57 | 28.76 | 6.76 | 41.14 | 21.95 | 13.20 | 19.19 |
| KHCO3 | 15.41 | 16.03 | 3.50 | 71.96 | 13.95 | 5.65 | 58.01 |
| KHCO3 | 79.28 | 23.32 | 5.02 | 49.05 | 20.01 | 12.11 | 29.04 |
| NH4HCO3 | 3.79 | 16.62 | 10.03 | 58.58 | 16.89 | 5.28 | 41.69 |
| NH4HCO3 | 4.35 | 16.32 | 9.89 | 58.39 | 16.55 | 6.21 | 41.84 |

TABLE III-continued

| | | | | | | | |
|---|---|---|---|---|---|---|---|
| Na$_2$CO$_3$ | 20.00 | 16.25 | 3.75 | 70.10 | 13.10 | 5.35 | 57.00 |
| Na$_2$CO$_3$ | 95.94 | 30.13 | 9.30 | 31.53 | 23.47 | 15.96 | 8.06 |
| K$_2$CO$_3$ | 4.24 | 15.57 | 7.55 | 66.51 | 14.86 | 5.42 | 51.65 |
| K$_2$CO$_3$ | 8.71 | 19.75 | 8.15 | 55.57 | 15.73 | 7.58 | 39.84 |

(Part 3)

| Buffer | Wt. of Buffer | Temp. Degrees C. | % 1 alpha-terpinene | % 2 p-cymene | % Limonene | % 3 gamma-terpinenes | % 4 2,4-8-menthadiene | terpinolene |
|---|---|---|---|---|---|---|---|---|
| (NH$_4$)$_2$CO$_3$ | 0.3 | 100 | 1.04 | 0.47 | 93.17 | 1.06 | 0.43 | 3.19 |
| (NH$_4$)$_2$CO$_3$ | 0.3 | 140 | 2.02 | 0.77 | 90.05 | 1.60 | 0.73 | 3.82 |
| BaCO$_3$ | 0.3 | 100 | 0.32 | 0.17 | 97.76 | 0.22 | 0.06 | 1.20 |
| BaCO$_3$ | 0.3 | 140 | 1.44 | 0.40 | 90.90 | 0.88 | 0.28 | 5.50 |
| Li$_2$CO$_3$ | 0.3 | 100 | 0.87 | 0.18 | 94.11 | 0.59 | 0.19 | 3.88 |
| Li$_2$CO$_3$ | 0.3 | 140 | 22.27 | 2.30 | 16.09 | 17.71 | 11.19 | 24.52 |
| MgCO$_3$ | 0.3 | 100 | 1.60 | 0.37 | 89.58 | 1.36 | 0.51 | 6.09 |
| MgCO$_3$ | 0.3 | 140 | 20.49 | 3.75 | 17.73 | 17.10 | 10.14 | 24.06 |
| Ba(OH)$_2$ | 0.3 | 100 | 1.24 | 0.27 | 91.87 | 0.96 | 0.34 | 4.90 |
| Ba(OH)$_2$ | 0.3 | 140 | 12.15 | 1.31 | 39.76 | 9.71 | 5.18 | 28.58 |
| Sr(OH)$_2$ | 0.3 | 100 | 0.76 | 0.33 | 95.37 | 0.64 | 0.22 | 2.29 |
| Sr(OH)$_2$ | 0.3 | 140 | 2.32 | 0.57 | 87.14 | 1.80 | 0.84 | 6.38 |
| NaOH | 0.3 | 100 | 1.62 | 0.46 | 90.13 | 1.37 | 0.49 | 5.27 |
| NaOH | 0.3 | 140 | 2.18 | 0.51 | 85.65 | 1.95 | 0.78 | 8.19 |
| KOH | 0.3 | 100 | 0.43 | 0.21 | 97.21 | 0.29 | 0.09 | 1.50 |
| KOH | 0.3 | 140 | 0.46 | 0.21 | 96.88 | 0.34 | 0.11 | 1.72 |
| LiOH | 0.3 | 100 | 0.68 | 0.22 | 95.52 | 0.54 | 0.18 | 2.56 |
| LiOH | 0.3 | 140 | 2.10 | 0.45 | 85.08 | 1.53 | 0.51 | 9.55 |
| Ca(OH)$_2$ | 0.3 | 100 | 0.75 | 0.17 | 94.97 | 0.51 | 0.16 | 3.14 |
| Ca(OH)$_2$ | 0.3 | 140 | 4.01 | 0.28 | 72.93 | 2.80 | 0.99 | 17.80 |
| BaO | 0.3 | 100 | 1.03 | 0.21 | 92.81 | 0.75 | 0.24 | 4.65 |
| BaO | 0.3 | 140 | 8.01 | 0.74 | 53.01 | 6.63 | 3.12 | 26.66 |

(Part 4)

| Buffer | % Conversion | % 1 alpha-terpinene | % 2 p-cymene | % Selectivity for 3 & 5 | % 3 gamma-terpinene | % 4 2,4-8-menthadiene | % 5 terpinolene |
|---|---|---|---|---|---|---|---|
| (NH$_4$)$_2$CO$_3$ | 6.67 | 15.59 | 7.05 | 63.72 | 15.89 | 6.45 | 47.83 |
| (NH$_4$)$_2$CO$_3$ | 9.79 | 20.63 | 7.87 | 46.36 | 16.34 | 7.46 | 39.02 |
| BaCO$_3$ | 2.08 | 15.38 | 8.17 | 68.27 | 10.58 | 2.88 | 57.69 |
| BaCO$_3$ | 8.94 | 16.11 | 4.47 | 71.36 | 9.84 | 3.13 | 61.52 |
| Li$_2$CO$_3$ | 5.73 | 15.18 | 3.14 | 78.01 | 10.30 | 3.32 | 67.71 |
| Li$_2$CO$_3$ | 83.75 | 26.59 | 2.75 | 50.43 | 21.15 | 13.36 | 29.28 |
| MgCO$_3$ | 10.26 | 15.59 | 3.61 | 72.62 | 13.26 | 5.97 | 59.36 |
| MgCO$_3$ | 82.11 | 24.94 | 4.57 | 50.13 | 20.83 | 12.35 | 29.30 |
| Ba(OH)$_2$ | 7.97 | 15.56 | 3.39 | 73.53 | 12.05 | 4.27 | 61.48 |
| Ba(OH)$_2$ | 60.08 | 20.22 | 2.18 | 63.73 | 16.16 | 8.62 | 47.57 |
| Sr(OH)$_2$ | 4.47 | 17.00 | 7.38 | 65.55 | 14.32 | 4.92 | 51.23 |
| Sr(OH)$_2$ | 12.70 | 18.27 | 4.49 | 64.41 | 14.17 | 6.61 | 50.24 |
| NaOH | 9.71 | 16.68 | 4.74 | 68.38 | 14.11 | 5.05 | 54.27 |
| NaOH | 14.19 | 15.36 | 3.59 | 71.46 | 13.74 | 5.50 | 57.72 |
| KOH | 2.63 | 16.35 | 7.98 | 68.06 | 11.03 | 3.42 | 57.03 |
| KOH | 2.96 | 15.54 | 7.09 | 69.60 | 11.49 | 3.72 | 58.11 |
| LiOH | 4.32 | 15.74 | 6.09 | 63.76 | 12.50 | 4.17 | 59.26 |
| LiOH | 14.76 | 14.23 | 3.05 | 75.07 | 10.37 | 3.46 | 64.70 |
| Ca(OH)$_2$ | 4.87 | 15.40 | 3.49 | 74.95 | 10.47 | 3.29 | 64.48 |
| Ca(OH)$_2$ | 26.91 | 14.90 | 1.04 | 76.56 | 10.41 | 3.68 | 66.15 |
| BaO | 7.03 | 14.65 | 2.99 | 76.82 | 10.67 | 3.41 | 66.15 |
| BaO | 46.83 | 17.10 | 1.58 | 71.09 | 14.16 | 6.66 | 56.93 |

(Part 5)

| Buffer | Wt. of Buffer | Temp. Degrees C. | % 1 alpha-terpinene | % 2 p-cymene | % Limonene | % 3 gamma-terpinenes | % 4 2,4-8-menthadiene | terpinolene |
|---|---|---|---|---|---|---|---|---|
| MgO | 0.3 | 100 | 0.79 | 0.23 | 94.92 | 0.61 | 0.17 | 2.99 |
| MgO | 0.3 | 140 | 4.21 | 0.50 | 71.95 | 3.21 | 1.30 | 17.57 |
| CaO | 0.3 | 100 | 0.49 | 0.15 | 96.86 | 0.30 | 0.08 | 1.89 |
| CaO | 0.3 | 140 | 3.00 | 0.27 | 78.00 | 2.05 | 0.64 | 15.11 |
| Ca Stearate | 0.3 | 100 | 0.66 | 0.26 | 95.57 | 0.58 | 0.25 | 2.28 |
| Ca Stearate | 0.3 | 140 | 1.87 | 0.53 | 90.33 | 1.46 | 0.80 | 4.46 |
| K Stearate | 0.3 | 100 | 0.23 | 0.12 | 98.32 | 0.13 | 0.03 | 0.96 |
| K Stearate | 0.3 | 140 | 0.27 | 0.17 | 97.96 | 0.15 | 0.03 | 1.19 |

(Part 6)

| Buffer | % Conversion | % 1 alpha-terpinene | % 2 p-cymene | % Selectivity for 3 & 5 | % 3 gamma-terpinene | % 4 2,4-8-menthadiene | % 5 terpinolene |
|---|---|---|---|---|---|---|---|
| MgO | 4.92 | 16.06 | 4.67 | 73.17 | 12.40 | 3.46 | 60.77 |
| MgO | 27.89 | 15.10 | 1.79 | 74.51 | 11.51 | 4.66 | 63.00 |
| CaO | 2.98 | 16.44 | 5.03 | 73.49 | 10.07 | 2.68 | 63.42 |
| CaO | 21.84 | 13.74 | 1.24 | 78.57 | 9.39 | 2.93 | 69.18 |
| Ca Stearate | 4.27 | 15.46 | 6.09 | 66.98 | 13.58 | 5.86 | 53.40 |
| Ca Stearate | 9.51 | 19.66 | 5.57 | 62.25 | 15.35 | 8.41 | 46.90 |
| K Stearate | 1.52 | 15.13 | 7.89 | 71.71 | 8.55 | 1.97 | 63.16 |
| K Stearate | 1.88 | 14.36 | 9.04 | 71.28 | 7.98 | 1.60 | 63.30 |

The examples set forth above in Tables I, II and III were run without added solvent. Solvent or diluent may be included if desired, for example, to aid in temperature control by providing a reflux point. When the isomerization is run without any buffer, but with heptane solvent (100 degrees C.) isomerization does occur after 4 hours; but mainly dimers are obtained and only limited dienes. The catalyst is not reusable in unreconditioned form.

It is convenient to give a specific example of a preferred catalyst. Any orthotitanic acid catalyst may be used herein; but best results have been secured with the catalyst prepared as follows:

961 g. of deionized water was charged to a 2-liter 3-necked flask equipped with a thermometer, agitator, and reflux condenser. 336 g. NaOH pellets were added slowly until dissolved. The caustic concentration should be 25%±1% (max. 28%). 100 g. anatase $TiO_2$ were added over a 15 minute period with stirring. The contents of the flask were heated to reflux ($\sim$112°–115° C.) and held for 8 hours. Good agitation is required. A superatmospheric pressure of 5–25 psi is preferred for this digestion.

The flask and contents were cooled to room temperature and vacuum filtered on a Buchner funnel. The cake (1.5–2 inches thick) was washed with deionized water (20 times the weight of $TiO_2$) until the filtrate showed a pH of $\leq$10.5.

Vacuum was then pulled on the filter cake until the cake just cracked, and the cake was then reslurried in deionized water. The cake was not air dried.

Formic acid (90%) was added slowly to the slurry until pH of 2.5. Stirring was continued for 45–60 minutes. The pH was maintained at 2.5 by adding formic acid when necessary. Typically 10 to 20 g. of acid were used.

The product was filtered and washed with deionized water until a pH of 5.5 is obtained ($\sim$6 hours using 20 times the weight of $TiO_2$). The product was not air dried. The catalyst is then conditioned by heating at 500° C. for 3 hours or 120° C. for 24 hours. The conditioned product was used in the foregoing specific examples. Orthotitanic acid of this example is soluble in dilute $H_2SO_4$ or HCl and is amorphous to X-ray. Metatitanic acid, on the contrary is soluble only with difficulty in hot concentrated $H_2SO_4$, and is also amorphous to X-ray.

What is claimed is:

1. A process for isomerizing limonene to terpinolene at a temperature of from 75 degrees C. to 200 degrees C. in the presence of a catalytic amount of orthotitanic acid catalyst which is characterized by the inclusion in the isomerization mass of less than 2% by weight of the catalyst of a buffer selected from alkali metal or alkaline earth metal or ammonium acetates, carbonates, bicarbonates, citrates, hydroxides, oxides, phosphates, acid phosphates, and stearates.

2. A process as defined in claim 1 wherein the amount of buffer is in the range of 0.05% to 2% by weight of the limonene charge.

3. A process as defined in claim 1 wherein the amount of buffer is in the range of 0.1% to 1.0% by weight of the limonene charge.

4. A process as defined in claim 1 wherein the amount of buffer is in the range of from 0.2% to 0.5% by weight of the limonene charge.

5. A process as defined in claim 1 wherein the buffer is sodium acetate.

6. A process as defined in claim 4 wherein the buffer is sodium acetate.

7. A process as defined in claim 1 characterized in that the isomerization time is in the range of from 1 to 21.5 hours.

8. A process as defined in claim 6 characterized in that the isomerization time is in the range of from 3 to 4 hours.

* * * * *